United States Patent [19]
Orvik

[11] Patent Number: 4,739,070
[45] Date of Patent: Apr. 19, 1988

[54] PREPARATION OF SUBSTITUTED (DICHLOROMETHYL)PYRIDINES

[75] Inventor: Jon A. Orvik, Walnut Creek, Calif.

[73] Assignee: The Dow Chemical Company, Midland, Mich.

[21] Appl. No.: 855,226

[22] Filed: Apr. 23, 1986

[51] Int. Cl.⁴ .................. C07D 213/26; C07D 213/32
[52] U.S. Cl. ..................................... 546/345; 546/286; 546/288; 546/289; 546/295; 546/297; 546/304; 546/306
[58] Field of Search ............... 546/345, 346, 289, 286, 546/288, 295, 297, 304, 306

[56] References Cited

U.S. PATENT DOCUMENTS 4,172,203 10/1979 Ison ..................................... 546/345
4,260,766 4/1981 Morris ................................ 546/303
4,499,276 2/1985 Malhotra et al. .................... 546/346
4,499,277 2/1985 Malhotra et al. .................... 546/346

Primary Examiner—Alan L. Rotman

[57] ABSTRACT 2- and 4-(Dichloromethyl)pyridines containing electron withdrawing substituents on the ring are prepared by the reaction of the corresponding 2- or 4-halopyridines with excess chloroform in the presence of a strong base in a medium containing a dipolar aprotic solvent or a phase transfer catalyst. 3-Chloro-5-(trifluoromethyl)-2-(dichloromethyl)pyridine, for example, is prepared by the reaction of 2,3-dichloro-5-(trifluoromethyl)pyridine with chloroform in the presence of sodium hydroxide and N-methylpyrrolidone. Substituted 2-(dichloromethyl)pyridines are useful as agricultural pesticides and as intermediates for the preparation of agricultural pesticides.

16 Claims, No Drawings

PREPARATION OF SUBSTITUTED (DICHLOROMETHYL)PYRIDINES

BACKGROUND OF INVENTION

The present invention relates to a process for the preparation of certain substituted 2-(dichloromethyl)pyridines and substituted 4-(dichloromethyl)pyridines.

Various substituted 2- and 4-(dichloromethyl)pyridines are taught, for example, in U.S. Pat. Nos. 4,172,203, 4,260,766, and 4,499,277, to be useful variously as herbicides, fungicides and insecticides. In addition, they are known to be intermediates for the preparation of herbicides, fungicides, insecticides, plant growth regulators, and nitrification inhibitors as disclosed, for example, in U.S. Pat. Nos. 3,173,919, 3,591,596, 3,838,159, and 4,497,652, and in U.S. patent application Ser. No. 653,399 filed Sept. 24, 1984.

Substituted 2- and 4-(dichloromethyl)pyridines have previously been prepared by a variety of methods, such as the reduction of the corresponding substituted (trichloromethyl)pyridines using a wide variety of reducing agents and the direct chlorination of substituted gamma and alpha picolines. In either case the ultimate starting material is a substituted gamma or alpha picoline. In view of the economic value of these compounds, it is desirable to have additional methods for their preparation which utilize other readily available starting materials.

SUMMARY OF THE INVENTION

It has now been found that substituted 2-(dichloromethyl)pyridines and substituted 4-(dichloromethyl)pyridines which contain electron withdrawing ring substituents can be prepared by the reaction of correspondingly substituted 2-halopyridines and 4-halopyridines, respectively, with chloroform in the presence of a strong base and a facilitator.

The present invention involves a process for the preparation of (dichloromethyl)pyridines of the formula

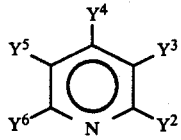
(I)

wherein
$Y^3$ and $Y^5$ each, independently represent H, F, Cl, Br, $CF_3$, $CHF_2$, $NO_2$, $CN$, $SO_2R$, or $SOR$;
$Y^2$, $Y^4$, and $Y^6$ each, independently represent H, F, Cl, Br, $CF_3$, $CHF_2$, $CHCl_2$, or $CN$; and
R represents $C_1$-$C_4$ alkyl; with the proviso that not more than two of $Y^2$, $Y^3$, $Y^4$, $Y^5$, and $Y^6$ represent H and at least one of $Y^2$, $Y^4$, and $Y^6$ represents $CHCl_2$
which comprises contacting a halopyridine of the formula

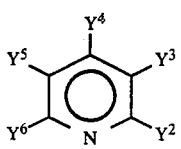
(II)

wherein
$Y^2$, $Y^3$, $Y^4$, $Y^5$, $Y^6$, and R are as defined hereinabove; with the proviso that not more than two of $Y^2$, $Y^3$, $Y^4$, $Y^5$, and $Y^6$ represent H and at least one of $Y^2$, $Y^4$, and $Y^6$ represents F, Cl, or Br
with chloroform in the presence of a strong base and one or more facilitators, which can be phase transfer catalysts, dipolar aprotic solvents, or mixtures thereof, under conditions conducive to the formation of the (dichloromethyl)pyridine compound. The (dichloromethyl)pyridine compound is recovered from the resulting mixture.

The reaction involved amounts to the replacement of a 2, 4, or 6 position halo (F, Cl, or Br) substituent of pyridine with a $CHCl_2$ moiety and can be illustrated as follows:

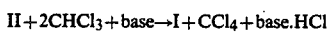

II + 2CHCl₃ + base → I + CCl₄ + base.HCl

DETAILED DESCRIPTION OF THE INVENTION

In carrying out the process of the present invention a compound of Formula II, chloroform, a strong base, and the facilitators are combined and allowed to react until a substantial amount of the compound of Formula II has reacted or until a substantial amount of a compound of Formula I has formed. Reaction times of 1 minute to 27 hours are typical depending on the reactants and the reaction conditions employed.

The reaction mixture components can be combined in any order, but it is often convenient to add the strong base last. The reaction is generally carried out with agitation at temperatures between about −20° C. and about 160° C. A temperature range of about 0° C. to about 80° C. is preferred and of about 20° C. to about 40° C. is especially preferred. It is preferred to carry out the reaction at atmospheric pressure, but the specific pressure employed is not critical.

Chloroform is consumed in the reaction of the process in the ratio of two moles per mole of compound of Formula II employed. Amounts about 2 to about 100 moles per mole of compound of Formula II are generally employed and from about 2.5 to about 10 moles are preferred. Any excess chloroform employed tends to drive the reaction toward completion.

The strong base is generally an alkali metal or quaternary ammonium hydroxide although any base which is sufficiently strong to convert a portion of the chloroform to its carbanion under the reaction conditions can be employed. Examples of useful bases include hydroxylic strong bases, such as sodium hydroxide, potassium hydroxide, benzyl trimethylammonium hydroxide, tetrabutylammonium hydroxide, and the like. The strong base can be added to the reaction mixture as a solid or as a solution in a solvent, such as water. In the latter case concentrations greater than 20 percent are preferred and concentrations greater than 40 percent are especially preferred. One equivalent of strong base per mole of compound of Formula II is consumed in the reaction, but an amount in excess of one equivalent is generally employed. About 1 to about 20 equivalents are typical and about 2 to about 5 equivalents is preferred.

The facilitator of the present invention is a substance that promotes contact between the reactants. Substances known to perform this function include dipolar aprotic solvents and phase transfer catalysts. Suitable dipolar aprotic solvents include N,N-dimethylformamide, N-methylpyrrolidone, N-formylmorpholine, dimethyl sulfoxide, sulfolane, and the like, and mixtures thereof. Such solvents are utilized in the reaction mixture in an effective amount, which is an amount sufficient to solubilize at least a portion of the strong base. Chloroform:dipolar aprotic solvent volume ratios of about 10:1 to 1:10 are generally useful, but it is often convenient to employ approximately equal amounts. In the case of phase transfer catalysts, which can be utilized alone or in conjunction with dipolar aprotic solvents, any known such catalyst or mixture of catalysts capable of transferring hydroxide ion into organic media can be employed. Quaternary ammonium halides, such as benzyl triethylammonium chloride, tetrabutylammonium bromide, and tricapryl methylammonium chloride, are preferred. Effective amounts are employed. Chloroform:phase transfer catalyst weight ratios of 200:1 to 10:1 are generally useful.

The reaction described hereinabove can be carried out employing either batch or continuous operations utilizing procedures known to those skilled in the art.

The substituted (dichloromethyl)pyridine compounds of Formula I prepared by the process of the present invention can be recovered by conventional means. For example, water can be added to quench the reaction and extract most of any dipolar aprotic solvent and at least some of any phase transfer catalyst and, after removing the aqueous phase that forms, the organic phase remaining can be distilled under reduced pressure to remove the excess chloroform and any low boiling constituents. The desired compound of Formula I, which is present in the residue, can be purified by further distillation under reduced pressure or, if it is a solid, by recrystallization from an appropriate solvent. Alternatively, the reaction mixture can be distilled under reduced pressure directly to remove the more volatile components and the desired compound of Formula I can be isolated from the residue obtained by extraction procedures, chromatography procedures, distillation procedures, and the like.

Substituted 2- and 4-(dichloromethyl)pyridines which can be prepared by the process of the present invention are illustrated by the compounds in the following table, the substituents of which refer to Formula I:

| Compound | $Y^2$ | $Y^3$ | $Y^4$ | $Y^5$ | $Y^6$ |
|---|---|---|---|---|---|
| 1 | $CHCl_2$ | Cl | H | Cl | Cl |
| 2 | $CHCl_2$ | Cl | H | H | Cl |
| 3 | $CHCl_2$ | Cl | H | Cl | H |
| 4 | $CHCl_2$ | F | CN | F | $CHCl_2$ |
| 5 | $CHCl_2$ | Cl | $CHCl_2$ | Cl | Cl |
| 6 | $CHCl_2$ | Cl | H | Cl | F |
| 7 | $CHCl_2$ | Cl | H | CN | F |
| 8 | $CHCl_2$ | Br | H | $NO_2$ | H |
| 9 | $CHCl_2$ | H | $CHF_2$ | $SO_2CH_3$ | H |
| 10 | $CHCl_2$ | Br | H | $SOC_4H_9$ | Br |
| 11 | $CHCl_2$ | Cl | H | $CF_3$ | H |
| 12 | $CHCl_2$ | F | H | $CF_3$ | H |
| 13 | $CHCl_2$ | $CF_3$ | H | $CF_3$ | Cl |
| 14 | $CHCl_2$ | $CF_3$ | H | H | Cl |
| 15 | $CHCl_2$ | $CF_3$ | H | Cl | Cl |
| 16 | $CHCl_2$ | H | $CF_3$ | H | Cl |
| 17 | $CHCl_2$ | Cl | $CF_3$ | Cl | Br |
| 18 | $CHCl_2$ | Br | $CF_3$ | Br | F |
| 19 | $CHCl_2$ | Cl | H | Cl | $CF_3$ |
| 20 | $CHCl_2$ | Br | H | Br | $CHF_2$ |
| 21 | Cl | Cl | $CHCl_2$ | Cl | Cl |
| 22 | CN | Cl | $CHCl_2$ | Cl | CN |
| 23 | $CHCl_2$ | Cl | $CHCl_2$ | Cl | $CHCl_2$ |
| 24 | $CF_3$ | H | $CHCl_2$ | H | $CF_3$ |

For those embodiments of the invention which utilize starting materials of Formula II wherein more than one of $Y^2$, $Y^4$, and $Y^6$ represents halo (F, Cl, or, Br), multiple products are generally obtained which correspond to the sequential reaction of each of the halo substituents in the 2, 4, and 6 positions of the ring according to the process of the invention. In addition, for those embodiments utilizing unsymmetrical starting materials of Formula II wherein $Y^2$ and $Y^6$ represent halo or utilizing starting materials wherein $Y^4$ and one or both of $Y^2$ and $Y^6$ represent halo, competitive reactions of the 2, 4, and 6 halogen atoms generally take place and a multiplicity of products is generally formed. Each of the products of Formula I produced in both of these circumstances is capable of being recovered from the resulting mixtures using chromatographic techniques, and in some cases the mixture can be employed without separation of the isomers and products. It is, however, normally preferable to utilize starting materials of Formula II wherein only one of $Y^2$, $Y^4$, and $Y^6$ represents halo or wherein $Y^2$ and $Y^6$ represent the same halo and $Y^4$ is other than halo.

The starting substituted halopyridines of Formula II are well known compounds and have been used extensively as starting materials in the art. Many examples and methods of preparation are reported in "Pyridine and its Derivatives", edited by E. Klingsberg and its supplements edited by R. A. Abramovitch; others are described in U.S. Pat. Nos. 4,479,001 and 3,682,938 and elsewhere.

The following examples are presented to illustrate the invention and should not be construed as limiting the scope.

EXAMPLE 1

Preparation of 3,5,6-trichloro-2-(dichloromethyl)pyridine (Cpd. 1 of table)

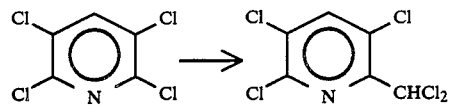

2,3,5,6-Tetrachloropyridine (1.1 g, 0.005 mole) was combined with 5 ml of N-methylpyrrolidine and 5 ml (about 0.062 mole) of chloroform in a reaction vessel and to the resulting solution 6 g of 50 percent aqueous sodium hydroxide (0.075 mole) was added with stirring. After 30 minutes the title compound was shown to be present in the reaction mixture by gas chromatography at approximately 15 percent conversion.

EXAMPLE 2

Preparation of 3,6-dichloro-2-(dichloromethyl)pyridine (Cpd. 2 of table)

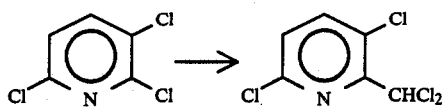

2,3,6-Trichloropyridine (1.0 g, 0.0055 mole) was combined with 4 g N-methylpyrrolidone, 4 g (0.033 mole) of chloroform, and 1.0 g of 50 percent aqueous sodium hydroxide (0.013 mole). The resulting mixture was stirred and warmed mildly for about 1 hour at which time the product was found to be present in the reaction mixture by gas chromatography and mass spectrometry using an authentic sample of the product as a standard. After standing overnight at ambient temperature the title compound represented about 1.7 percent of the pyridines in the mixture.

EXAMPLE 3

Preparation of 3-chloro-5-(trifluoromethyl)-2-(dichloromethyl)pyridine (Cpd. 11 of table)

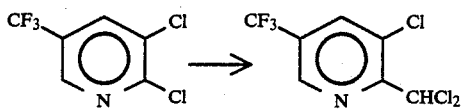

2,3-Dichloro-5-(trifluoromethyl)pyridine (43.2 g, 0.20 mole) was dissolved in 140 g (1.17 mole) of chloroform and 105 g of N-methylpyrrolidone. Sodium hydroxide (40 g of 50 percent aqueous solution, 0.5 mole) was added with stirring and the mixture was allowed to stir for 20 hours at room temperature. Another 10 g of 50 percent aqueous sodium hydroxide was added and stirring was continued. After 27 total hours a large excess of water was added. The resulting aqueous layer was removed and the organic layer was concentrated on a rotary evaporator under reduced pressure to obtain an oil containing the title compound. The oil was distilled in a fractionating column and the product fractions washed with dilute aqueous sodium carbonate to obtain 18.8 g of the title compound (35.5 percent of theory) having 97 percent purity by gas chromatography. The product, which was identified by its mass spectrum (parent peak at 263 mass units) and gas chromatographic parameters (compared with an authentic standard), had a boiling point of 108°–114° C. at 19 mm Hg pressure. Approximately 17.5 g of unreacted 2,3-dichloro-5-(trifluoromethyl)pyridine was also recovered.

I claim:

1. A process for the preparation of a (dichloromethyl)pyridine compound of the formula

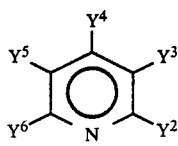

wherein $Y^3$ and $Y^5$ each, independently represents H, F, Cl, Br, $CF_3$, $CHF_2$, $NO_2$, CN, $SO_2R$, or SOR;

$Y^2$, $Y^4$, and $Y^6$ each, independently represents H, F, Cl, Br, $CF_3$, $CHF_2$, $CHCl_2$, or CN; and R represents $C_1$–$C_4$ alkyl;

with the proviso that not more than two of $Y^2$, $Y^3$, $Y^4$, $Y^5$, and $Y^6$ represent H and at least one of $Y^2$, $Y^4$, and $Y^6$ represents $CHCl_2$ which comprises contacting a halopyridine of the formula

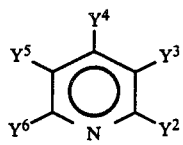

wherein $Y^2$, $Y^3$, $Y^4$, $Y^5$, $Y^6$, and R are as defined hereinabove; with the proviso that not more than two of $Y^2$, $Y^3$, $Y^4$, $Y^5$, and $Y^6$ represent H and at least one of $Y^2$, $Y^4$, and $Y^6$ represents F, Cl, or Br with chloroform in the presence of a strong base and at least one facilitator selected from the group consisting of phase transfer catalysts and dipolar aprotic solvents, under conditions conducive to the formation of the (dichloromethyl)pyridine compound by replacement of at least one 2-, 4-, or 6-position F, Cl, or Br substituent with a $CHCl_2$ moiety and, thereafter, recovering the (dichloromethyl)pyridine compound.

2. A process according to claim 1 wherein $Y^2$, $Y^3$, $Y^4$, $Y^5$, and $Y^6$ each, independently represents H, F, Cl, Br, $CF_3$, or CN.

3. A process according to claim 1 wherein only one of $Y^2$, $Y^4$, and $Y^6$ of the halopyridine represents F, Cl or Br.

4. A process according to claim 1 wherein a 6- or 2-(dichloromethyl)pyridine compound of claim 1 is prepared.

5. A process according to claim 4 wherein the (dichloromethyl)pyridine compound prepared is 3,6-dichloro-2-(dichloromethyl)pyridine.

6. A process according to claim 4 wherein the (dichloromethyl)pyridine compound prepared is 3,5,6-trichloro-2-(dichloromethyl)pyridine.

7. A process according to claim 4 wherein the (dichloromethyl)pyridine compound prepared is 3-chloro-5-(trifluoromethyl)-2-(dichloromethyl)pyridine.

8. A process according to claim 1 wherein the strong base is a strong hydroxylic base.

9. A process according to claim 8 wherein the strong hydroxylic base is sodium hydroxide or potassium hydroxide.

10. A process according to claim 9 wherein the strong hydroxylic base is sodium hydroxide.

11. A process according to claim 8 wherein the strong base is employed in an aqueous solution.

12. A process according to claim 1 wherein the facilitator is a dipolar aprotic solvent.

13. A process according to claim 12 wherein the dipolar aprotic solvent is N-methylpyrrolidone, dimethylformamide or dimethylsulfoxide.

14. A process according to claim 13 wherein the dipolar aprotic solvent is N-methylpyrrolidone.

15. A process according to claim 1 wherein the facilitator is a phase transfer catalyst.

16. A process according to claim 15 wherein the phase transfer catalyst is a quaternary ammonium halide.

* * * * *